US00PP18768P2

(12) United States Plant Patent
Saul

(10) Patent No.: US PP18,768 P2
(45) Date of Patent: Apr. 29, 2008

(54) ***ECHINACEA* PLANT NAMED 'EMILY SAUL'**

(50) Latin Name: ***Echinacea purpurea*×*Echinacea paradoxa***
Varietal Denomination: Emily Saul

(75) Inventor: Richard Saul, Cleveland, GA (US)

(73) Assignee: Itsaul Plants LLC, Atlanta, GA (US)

( * ) Notice: Subject to any disclaimer, the term of this patent is extended or adjusted under 35 U.S.C. 154(b) by 0 days.

(21) Appl. No.: 11/648,867

(22) Filed: Dec. 29, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Echinacea* plant named 'Emily Saul', characterized by its relatively compact, upright and columnar plant habit; freely branching habit; large single inflorescence with dark red purple-colored ray florets, relatively large inflorescence discs; and strong flowering stems that hold the inflorescences upright.

1 Drawing Sheet

Botanical designation: *Echinacea purpurea*×*Echinacea paradoxa.*
Cultivar denomination: 'EMILY SAUL'.

BACKGROUND OF THE INVENTION

The present invention relates to a new and distinct cultivar of *Echinacea* plant, botanically known as *Echinacea purpurea*×*Echinacea paradoxa,* and hereinafter referred to by the name 'Emily Saul'.

The new *Echinacea* originated from an open-pollination in July, 2002, of an unnamed selection of *Echinacea purpurea*×*Echinacea paradoxa,* not patented, as the female, or seed, parent with an unknown selection of *Echinacea purpurea*×*Echinacea paradoxa,* as the male, or pollen, parent. The new *Echinacea* was discovered and selected by the Inventor as a single flowering plant from within the progeny of the stated open-pollination grown in a controlled environment in Dahlonega, Ga., in June, 2003.

Asexual reproduction of the new *Echinacea* by tissue culture in a controlled environment in Atlanta, Ga. since August, 2004, has shown that the unique features of this new *Echinacea* are stable and reproduced true to type in successive generations.

SUMMARY OF THE INVENTION

The cultivar Emily Saul has not been observed under all possible environmental conditions. The phenotpye may vary somewhat with variations in environment such as temperature and light intensity, without, however, any variance in genotype.

The following traits have been repeatedly observed and are determined to be the unique characteristics of 'Emily Saul'. These characteristics in combination distinguish 'Emily Saul' as a new and distinct cultivar of *Echinacea:*

1. Relatively compact, upright and columnar plant habit.
2. Freely branching habit.
3. Large single inflorescences with dark red purple-colored ray florets.

4. Relatively large inflorescence discs.
5. Strong flowering stems that hold the inflorescences upright.

Compared to plants of the female parent selection, plants of the new *Echinacea* are more freely branching and differ in ray floret coloration.

Plants of the new *Echinacea* can be compared to plants of the *Echinacea* cultivar Magnus, not patented. In side-by-side comparisons conducted in Dahlonega, Ga., plants of the new *Echinacea* differed from plants of the cultivar Magnus in the following characteristics:

1. Plants of the new *Echinacea* were more compact than plants of the cultivar Magnus.
2. Plants of the new *Echinacea* and the cultivar Magnus differed in stem and leaf coloration.
3. Flowers of plants of the new *Echinacea* were more fragrant than flowers of plants of the cultivar Magnus.
4. Plants of the new *Echinacea* had larger flowers than plants of the cultivar Magnus.
5. Plants of the new *Echinacea* had darker red purple-colored ray florets than plants of the cultivar Magnus.

BRIEF DESCRIPTION OF THE PHOTOGRAPH

The accompanying photograph illustrates the overall appearance of the new *Echinacea.* The photograph show the colors as true as it is reasonably possible to obtain in colored reproductions of this type. Colors in the photograph may differ slightly from the color values cited in the detailed botanical description which accurately describe the colors of the new *Echinacea.* The photograph comprises a top perspective view of a typical flowering plant of 'Emily Saul' grown in a ground bed in an outdoor nursery.

DETAILED BOTANICAL DESCRIPTION

In the following description, color references are made to The Royal Horticultural Society Colour Chart, 1995 Editions, except where general terms of ordinary dictionary significance are used. The aforementioned photograph and following observations and measurements described plants grown in Dahlonega, Ga. during the spring and summer in an outdoor nursery and under conditions and practices which approximate those generally used in commercial *Echinacea* production. During the production of the plants, day temperatures ranged from about −5° C. to about 35° C. and night temperatures ranged from about −15° C. to about 21° C. Measurements and numerical values represent averages for typical flowering plants. Plants were about one year old when the photograph and description were taken.

Botanical classification: *Echinacea purpurea*×*Echinacea paradoxa* cultivar Emily Saul.

Parentage:

*Female parent.*—Unnamed selection of *Echinacea purpurea*×*Echinacea paradoxa,* not patented.

*Male parent.*—Unknown selection of *Echinacea purpurea*×*Echinacea paradoxa,* not patented.

Propagation:

*Type.*—By tissue culture.

*Time to initiate roots.*—About two weeks at 21° C.

*Time to produce a rooted young plant, summer.*—About 45 days at 29° C.

*Time to produce a rooted young plant, winter.*—About 60 days at 21° C.

*Root description.*—Thick; white in color.

*Rooting habit.*—Freely branching; moderately dense.

Plant description:

*Plant form/growth habit.*—Relatively compact, upright and columnar plant habit; freely basal branching with about seven basal branches; terminal inflorescences held upright on strong peduncles. Moderately vigorous growth habit.

*Plant height.*—About 28 cm.

*Plant diameter or spread.*—About 23 cm.

*Basal branches.*—Length: About 28 cm. Diameter: About 1 cm. Internode length: About 5.5 cm. Aspect: Upright. Strength: Strong. Texture: Smooth, glabrous. Color: 146A overlain with 183A.

Foliage description:

*Arrangement.*—Alternate, simple.

*Length.*—About 14.75 cm.

*Width.*—About 5.6 cm.

*Shape.*—Lanceolate.

*Apex.*—Acute; tapering.

*Base.*—Attenuate.

*Margin.*—Irregularly dentate; indentations shallow and widely-spaced.

*Texture, upper and lower surfaces.*—Pubescent; rough.

*Venation pattern.*—Pinnate.

*Color.*—Developing and fully expanded foliage, upper surface: Darker than 147A; venation, close to 147B. Developing and fully expanded foliage, lower surface: Darker and more green than 147B; lateral veins, close to 147B; midvein, close to 150D.

*Petiole.*—Length: About 8.5 cm. Diameter, at leaf base: About 5 mm. Diameter, at stem attachment: About 1 cm. Texture, upper and lower surfaces: Smooth, glabrous. Color, upper and lower surfaces: 147B to 147C; towards the stem, tinted with 183A.

Inflorescence description:

*Appearance.*—Rotate single inflorescence form with ray and disc florets. Inflorescences mostly terminal; occasional axially inflorescence development at upper leaf axils; inflorescences held upright on strong peduncles. Inflorescences persistent.

*Fragrance.*—Moderate; sweet.

*Time to flower.*—Plants flower continuously from the spring through the summer in Georgia.

*Inflorescence longevity.*—Inflorescences maintain good substance for about two weeks on the plant.

*Inflorescence bud.*—Height: About 8 mm. Diameter: About 1 cm. Shape: Oblate. Color: Close to 147A.

*Inflorescence size.*—Diameter: About 8.75 cm. Depth (height): About 2 cm. Disc diameter: Large, about 4 cm. Receptacle height: About 1.2 cm. Receptacle diameter: About 1.5 cm. Receptacle color: Close to 155D.

*Ray florets.*—Length: About 3.75 cm. Width: About 1 cm. Shape: Elongated oblong. Apex: Emarginate. Base: Attenuate; fused into a short corolla tube. Texture, upper and lower surfaces: Smooth, glabrous. Number of ray florets per inflorescence: About 20 arranged in a single whorl. Aspect: Horizontal to drooping or slightly reflexed. Color: When opening, upper surface: Close to 61A. When opening, lower surface: Close to 61B. Fully opened, upper surface: Close to 61B. Fully opened, lower surface: Close to 62A underlain with close to 61A.

*Disc florets.*—Shape: Tubular; apex five-pointed. Length: About 9 mm. Diameter: About 2 mm. Number of disc florets per inflorescence: About 230. Texture: Smooth, glabrous. Color: Immature: 144A. Mature: Apex: 183A. Mid-section: 144A. Base: 155D.

*Receptacle spines.*—Quantity: One per disc floret. Length: About 1.5 cm. Width: About 1 mm. Shape: Acicular. Apex: Sharply acute. Base: Tapering. Texture: Smooth, glabrous. Color: Apex: 187A; at the very apex, close to 25A. Mid-section: 144A. Base: 155D.

*Phyllaries.*—Quantity per inflorescence: About 60 in about three or four whorls. Length: About 1.5 cm. Width: About 5 mm. Shape: Linear to lanceolate. Apex: Acute. Base: Truncate. Margin: Entire. Texture, upper and lower surfaces: Pubescent. Color, upper and lower surfaces: 147A; towards the base, 146A.

*Reproductive organs.*—Androecium: Stamens per disc floret: One. Filament length: About 9 mm. Filament color: Close to 145D. Anther shape: Oblong. Anther length: Less than 1 mm. Anther color: Close to 146B to 146C. Pollen amount: Scarce. Pollen color: Close to 12A. Gynoecium: Pistil length: About 4 mm. Stigma shape: Cleft; reflexed. Stigma color: Close to 150D. Style length: About 3 mm. Style color: Close to 150D. Ovary color: Close to 157D. Seeds/fruits: Seed and fruit development have not been observed on plants of the new *Echinacea.*

Disease/pest resistance: Plants of the new *Echinacea* have not been shown to be resistant to pathogens and pests common to *Echinacea.*

Temperature tolerance: Plants of the new *Echinacea* have been observed to tolerate temperatures from about −15° C. to about 35° C.

It is claimed:

1. A new and distinct *Echinacea* plant named 'Emily Saul' as illustrated and described.

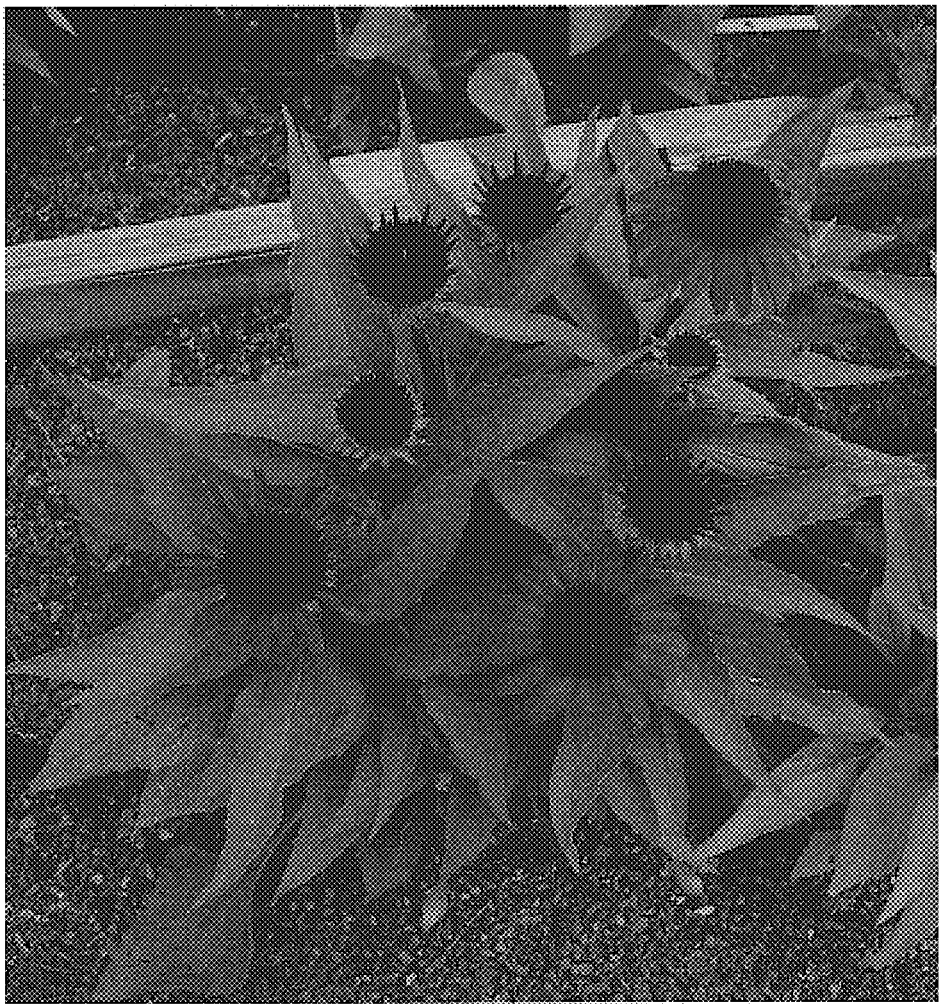

* * * * *